(12) United States Patent
Ryan et al.

(10) Patent No.: US 7,135,018 B2
(45) Date of Patent: Nov. 14, 2006

(54) ELECTROSURGICAL INSTRUMENT AND METHOD FOR TRANSECTING AN ORGAN

(75) Inventors: Thomas Ryan, Flemington, NJ (US); Rebecca Leibowitz, Scotch Plains, NJ (US); Roddi J. Simpson, Watchung, NJ (US); James S. Gatewood, Chesapeake, VA (US)

(73) Assignee: Ethicon, Inc., Somerville, NJ (US)

( * ) Notice: Subject to any disclaimer, the term of this patent is extended or adjusted under 35 U.S.C. 154(b) by 172 days.

(21) Appl. No.: 10/674,453

(22) Filed: Sep. 30, 2003

(65) Prior Publication Data

US 2005/0070895 A1    Mar. 31, 2005

(51) Int. Cl.
*A61F 18/04* (2006.01)
(52) U.S. Cl. .............. 606/48; 606/45; 606/46; 606/47; 606/48; 606/49; 606/50
(58) Field of Classification Search ............ 606/45–50, 606/167, 169–171, 113, 114, 201, 203
See application file for complete search history.

(56) References Cited

U.S. PATENT DOCUMENTS

| | | | | | |
|---|---|---|---|---|---|
| 3,739,784 | A | * | 6/1973 | Itoh | 606/113 |
| 4,493,320 | A | * | 1/1985 | Treat | 606/47 |
| 4,905,691 | A | * | 3/1990 | Rydell | 606/47 |
| 5,290,284 | A | * | 3/1994 | Adair | 606/37 |
| 5,746,747 | A | * | 5/1998 | McKeating | 606/114 |
| 5,782,839 | A | * | 7/1998 | Hart et al. | 606/113 |
| 5,919,191 | A | * | 7/1999 | Lennox et al. | 606/48 |
| 5,976,129 | A | * | 11/1999 | Desai | 606/40 |
| 6,176,858 | B1 | | 1/2001 | Dequesne et al. | |
| 6,494,881 | B1 | * | 12/2002 | Bales et al. | 606/45 |
| 6,616,654 | B1 | * | 9/2003 | Mollenauer | 606/28 |

* cited by examiner

*Primary Examiner*—Eduardo C Robert
*Assistant Examiner*—Christopher Prone

(57) ABSTRACT

An electrosurgical instrument and method is provided for transecting an organ. The electrosurgical instrument includes an introducer having a channel therein, and a conductive wire positioned in and deployable from the channel. A deployment device on the introducer is capable of moving the conductive wire between an undeployed position wherein it is substantially positioned within the channel, and a deployed position wherein a portion is deployed from and positioned outside of the channel and has a substantially looped configuration. A capture element at the distal end of the introducer can secure the distal end of the wire to the introducer, and the deployment device can subsequently move the wire toward the undeployed position to thereby cinch the conductive wire.

15 Claims, 9 Drawing Sheets

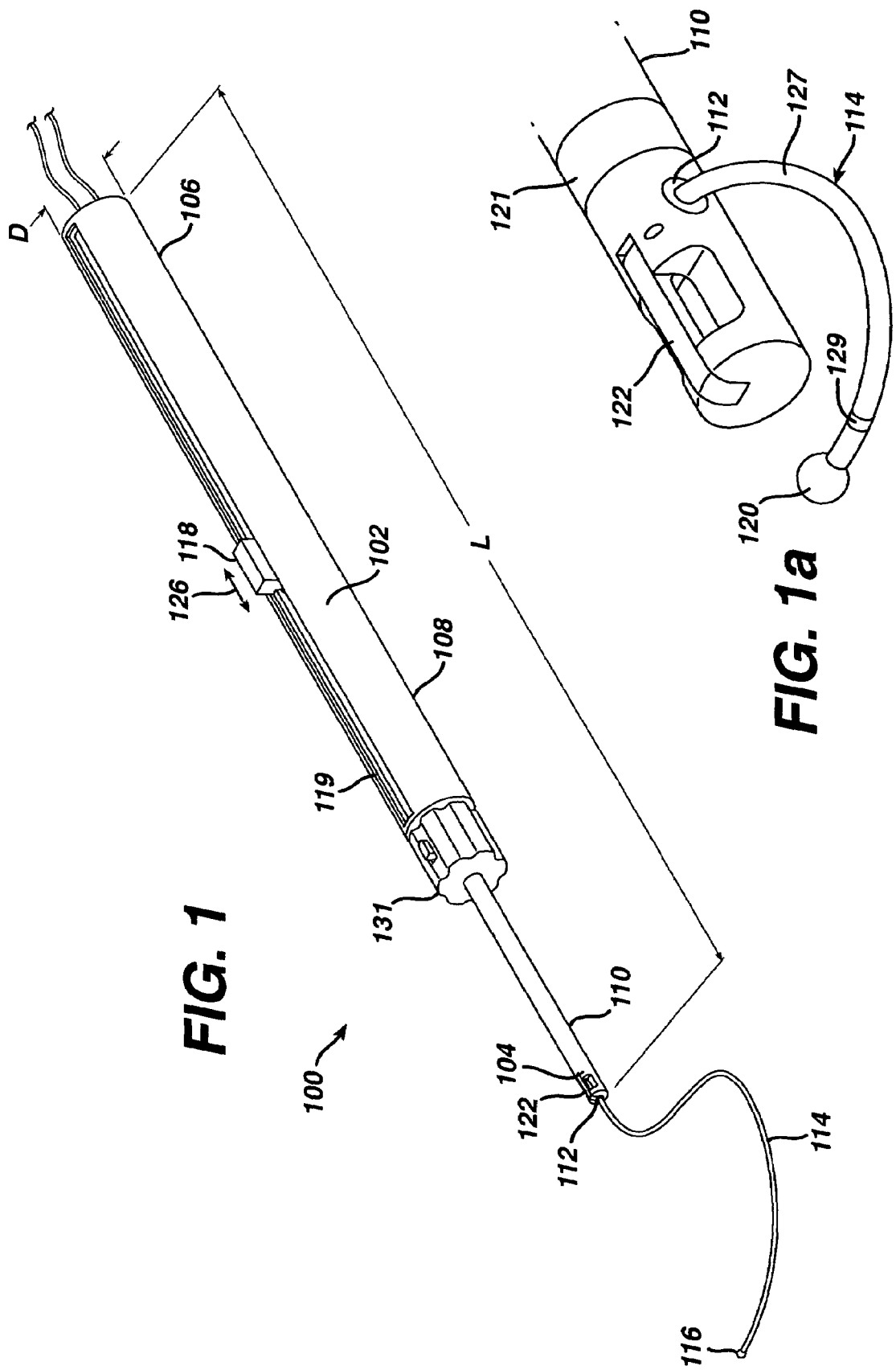

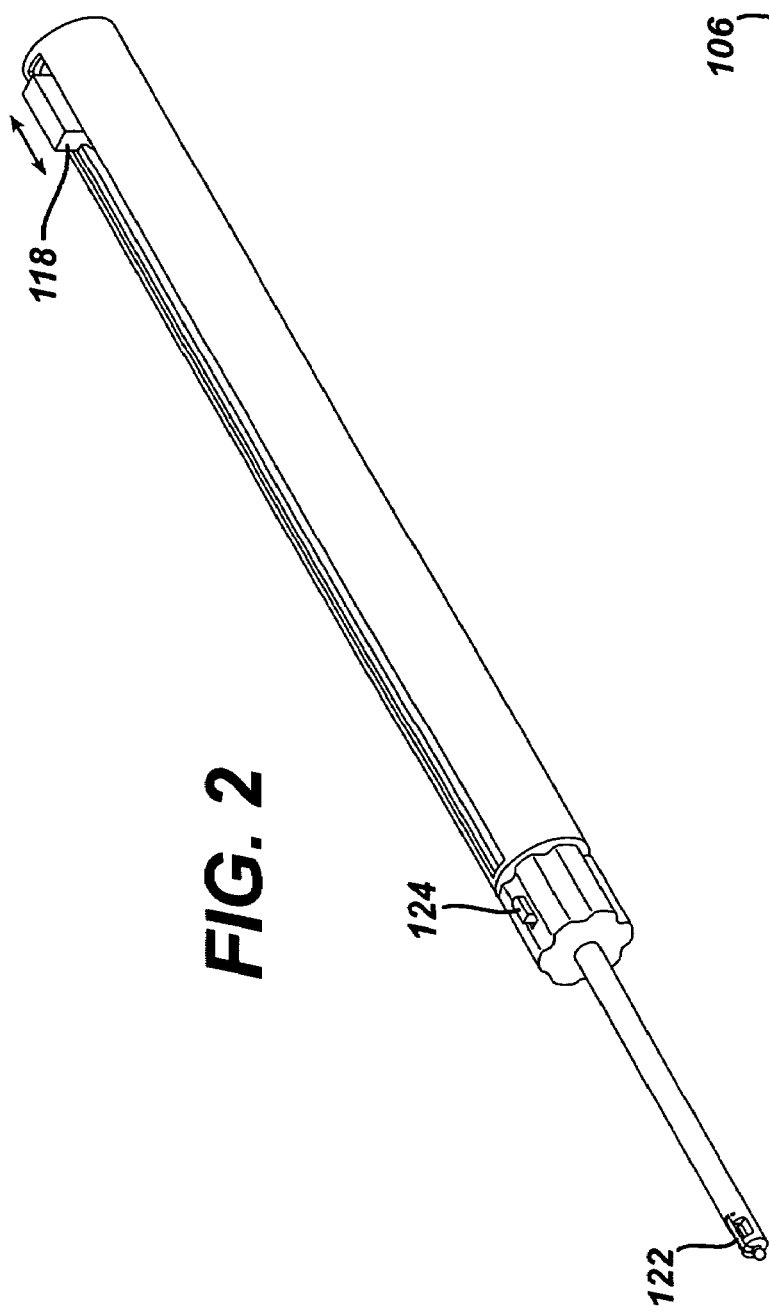
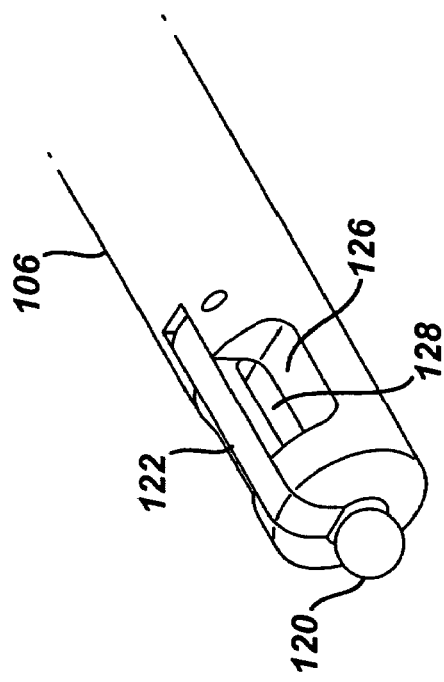

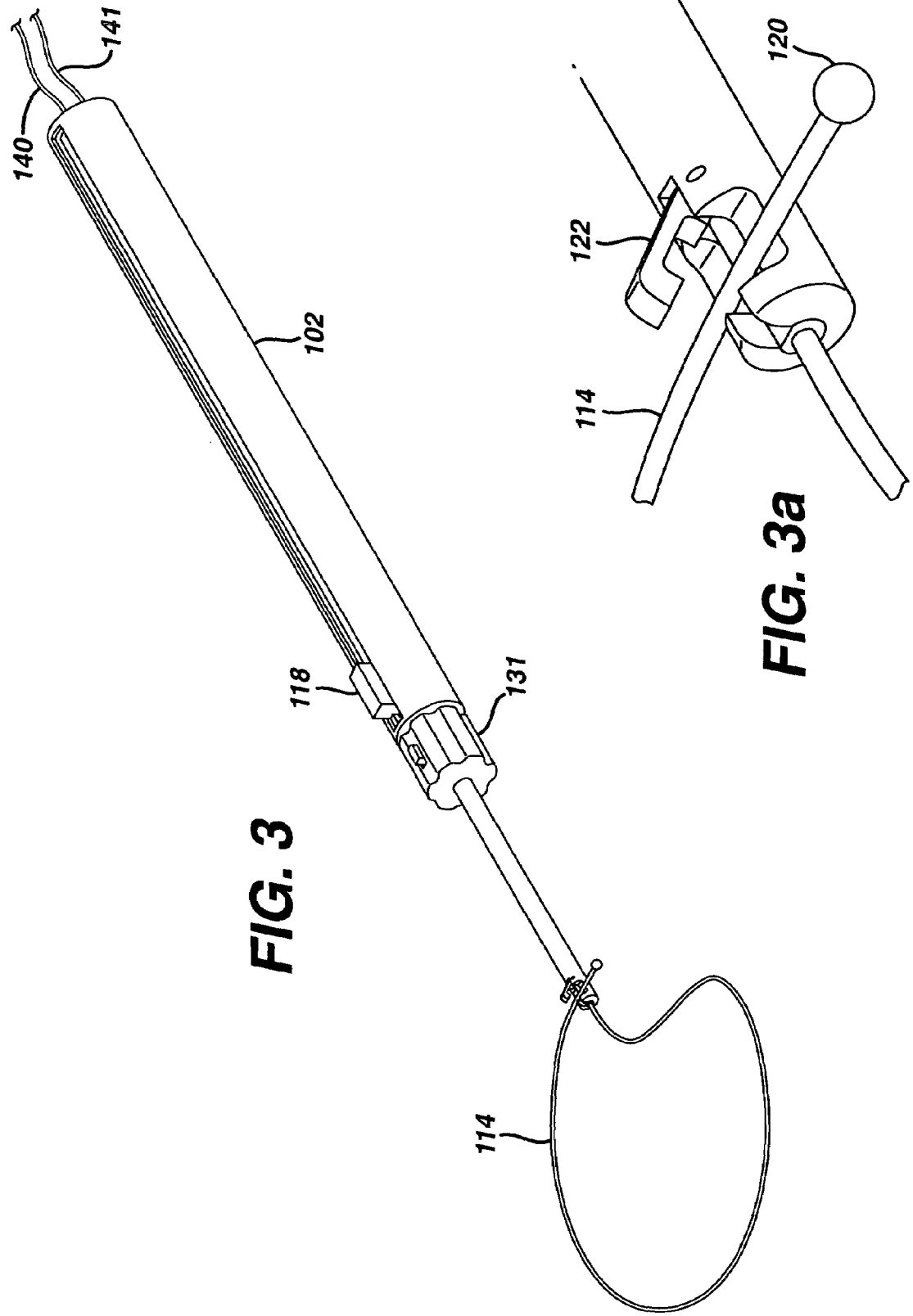

ELECTROSURGICAL INSTRUMENT AND METHOD FOR TRANSECTING AN ORGAN

BACKGROUND OF THE INVENTION

1. Field of the Invention

The present invention relates generally to electrosurgical instruments, and more particularly to electrosurgical instruments having particular application for transecting organs, such as the cervix during a supracervical hysterectomy.

2. Background Discussion

There are approximately 650,000 hysterectomies performed each year in the United States, with 75% of these being abdominal hysterectomies and only 25% being vaginal hysterectomies. An abdominal hysterectomy is the removal of the uterus with or without the ovaries through an incision in the abdomen. A vaginal hysterectomy is the removal of the uterus with or without the ovaries through an incision in the vaginal area. Laparoscopic supracervical hysterectomy (LSH) is one alternative to total abdominal hysterectomy. In an LSH procedure, the uterus is removed using a laparoscope, but unlike in a total laparoscopic hysterectomy, the cervix is left in place.

Some of the potential advantages of laparoscopic supracervical hysterectomy include a shorter operation time, fewer complications, and an earlier return to normal activity, including sexual activity. A difficult part of the procedure, however, is the amputation or transection of the uterine cervix from the fundus, as the uterus is quite mobile and difficult to stabilize. The uterus does not provide much resistance to pressure during amputation, and, therefore, requires some type of traction during resection. Further, conditions are often far from optimal due to the angle of approach with the cutting electrode or scissors, and the proximity of neighboring crucial structures that are sometimes difficult to keep at a distance. Because of these difficulties, amputation of the cervix often takes from 30–45 minutes, or nearly half of the time of the entire procedure. The difficulty and length of time associated with performing this part of the procedure has caused reluctance among many physicians to adopt the procedure.

Current methods and devices used for transecting the cervix during an LSH procedure include bipolar needles, cutting diathermy, morcellator knife, laser energy, blunt scissors, monopolar energy with scissors, harmonic scalpel (ultrasonic excision), and reverse cervical conization. All of these known devices and methods suffer from similar drawbacks in that they do not provide a means for rapid and effective transection. This is primarily due to the fact that the cervix is more fibrous than tissues typically encountered, and thus is difficult to cut. Further, due to the mobility of the uterus, these devices and methods do not enable the surgeon to reliably and effectively maintain a transverse cutting plane at the desired location during resection. This is important because if the transection is made too high (too close to the uterus), some endometrium may remain, causing the patient to have a menstrual period even though her uterus has been removed.

Another known device and method for transecting the cervix during an LSH procedure is described in U.S. Pat. No. 6,176,858. The '858 patent describes a monopolar electrosurgical cutting instrument having a conducting wire that forms a loop around the organ to be amputated, and subsequently amputates the organ by applying high frequency monopolar current through the wire. The disclosed cutting apparatus includes insulated portions at each end of the wire that both must be grasped by a grasper. The graspers must be manually moved to manipulate the wire around the cervical neck to thereby encircle it. Then, the energized wire is pulled through the cervical neck by pulling on the grasper, which in turn pulls on the wire loop. One of the drawbacks of this device is that it utilizes monopolar energy, which requires careful attention to insulating all but the cutting portion of the wire from surrounding tissue, and therefore, requires a complicated insulated tube and introducer mechanism. Further, the use of monopolar energy does not adequately control the dispersion of energy in and around the device. Another drawback of this device is that to achieve amputation, pressure must be exerted by the wire on the organ and the wire displaced or moved in the cutting direction to transect the cervix. In other words, the wire must be pulled in a single direction against the resistance of the cervical neck to transect it. Thus, unnecessary movement of the organs and tissue occurs, which potentially can lead to inadvertent damage of these structures. In addition, such movement is particularly problematic given the mobility of, and need to stabilize the uterus as described above. The device of the '858 patent exerts significant unidirectional force on the cervical neck, and provides no means to stabilize the organs.

Accordingly, there is a need for an improved system and method for performing organ transection. There is a particular need for a surgical instrument and method for performing an LSH procedure that reduces surgical time and that is safer and easier to perform.

SUMMARY OF THE INVENTION

The present invention provides an electrosurgical instrument for transecting an organ including an introducer having a distal end, a proximal end, and a channel therein extending to an opening at the distal end; a conductive wire slidably receivable within the channel and movable between an undeployed position wherein the conductive wire is substantially positioned within the channel and a deployed position wherein a portion of the conductive wire is deployed from and positioned outside of the introducer, and wherein in the deployed position the portion of the conductive wire has a substantially looped configuration. The instrument further includes a deployment device movably coupled to the introducer and movable between a first position and a second position. The deployment device is engaged with the conductive wire such that movement of the deployment device between the first and second positions causes the conductive wire to move between the undeployed and deployed positions. In addition, a capture element is located at a distal end of the introducer for securing the distal end of the conductive wire to the introducer when the conductive wire is in the deployed position. When the conductive wire is in the deployed position and when the distal end of the conductive wire is secured to the introducer by the capture element, the deployment device is movable toward the first position to thereby cinch the conductive wire substantially without moving the introducer.

According to one embodiment, the electrosurgical instrument is a bipolar instrument and the introducer further includes a conductive portion, wherein the conductive wire is an active electrode and the conductive portion of the introducer is a return electrode. In yet another embodiment, the instrument further includes a bipolar generator having a first pole electrically coupled to the active electrode and a second pole electrically coupled to the return electrode.

In alternate embodiments the conductive wire is made from a shape memory alloy, such as nitinol, whereas in another it is made of a spring steel.

In yet another embodiment, the capture element is movable between open and closed positions, and the instrument further includes a capture element actuator coupled with the capture element and movably coupled with the introducer. The capture element actuator is movable between first and second positions wherein such moving causes the capture element to move between the closed and open positions respectively. In one embodiment, the actuator element pivots about a pivot point to move between the open and closed positions.

In still another embodiment, the distal end of the introducer further includes a recess therein positioned relative to the capture element so that the capture element extends over the recess when in the closed position. It may be that when the distal end of the conductive wire is secured to the introducer by the capture element, it is positioned within the groove.

According to yet another embodiment, the introducer has a groove therein along a portion of its length, and the deployment device is slidably positioned within the groove.

In yet another embodiment, the introducer further includes a shaft extension portion having a first diameter and a handle portion adjacent the shaft extension portion having a second diameter greater than the first diameter. The channel extends through the shaft extension portion and into the handle portion. In yet another embodiment, the conductive wire further comprises a protrusion at the distal end.

Also provided is a bipolar electrosurgical instrument for transecting an organ that includes an introducer having a distal end, a proximal end, and a channel therein extending to an opening at the distal end, wherein the introducer has a conductive portion forming a return electrode, and a conductive wire made of a shape memory alloy slidably receivable within the channel and movable between an undeployed position wherein the conductive wire is substantially positioned within the channel and a deployed position wherein a portion of the conductive wire is deployed from and positioned outside of the introducer. When in the deployed position, the portion of the conductive wire has a substantially looped configuration, the conductive wire forming an active electrode. The instrument further includes a deployment device movably coupled to the introducer and movable between a first position and a second position. The deployment device is engaged with the conductive wire such that movement of the deployment device between the first and second positions causes the conductive wire to move between the undeployed and deployed positions respectively. Also included in the instrument is a capture element at a distal end of the introducer for securing the distal end of the conductive wire to the introducer when the conductive wire is in the deployed position. When the conductive wire is in the deployed position and when the distal end of the conductive wire is secured to the introducer by the capture element, the deployment device is movable toward the first position to thereby cinch the conductive wire substantially without moving the introducer.

A method for electrosurgically transecting an organ is also provided. The method includes the steps of providing an introducer having a proximal end, a distal end, and a channel therein extending to an opening at the distal end of the introducer, a conductive wire slidably receivable within the channel, a deployment device engaged with the conductive wire and movably coupled to the introducer and movable between first and second positions. Movement between the first and second positions moves the conductive wire between an undeployed position wherein the conductive wire is substantially positioned within the channel and a deployed position wherein a portion of the conductive wire is deployed from and positioned outside of the introducer and has a substantially looped configuration. The introducer further has a capture element at a distal end for securing a distal end of the electrosurgical wire to the introducer. The method also includes the steps of, with the conductive wire in the undeployed position, moving the distal end of the introducer adjacent a target organ to be transected, moving the deployment device from the first to second positions to thereby move the conductive wire to the deployed position, using the capture element to secure a distal end of the conductive wire to the introducer, applying radio frequency energy to the conductive wire, and moving the deployment device toward the first position to cinch the organ and thereby transect it.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIG. 1 is a perspective view of an electrosurgical instrument according to the present invention;

FIG. 1a illustrates an alternate embodiment of the distal end of an electrosurgical instrument according to the present invention;

FIG. 2 is a perspective view of the electrosurgical instrument of FIG. 1 with the electrosurgical wire in a retracted position;

FIG. 2a is a perspective view of the distal tip of the electrosurgical instrument of FIG. 2;

FIG. 3 is a perspective view of the electrosurgical instrument of FIG. 1 with the electrosurgical wire in a fully deployed position and the capture arm in the open position;

FIG. 3a is a perspective view of the distal end of the electrosurgical instrument of FIG. 3;

DETAILED DESCRIPTION OF THE INVENTION

Figure 3B:
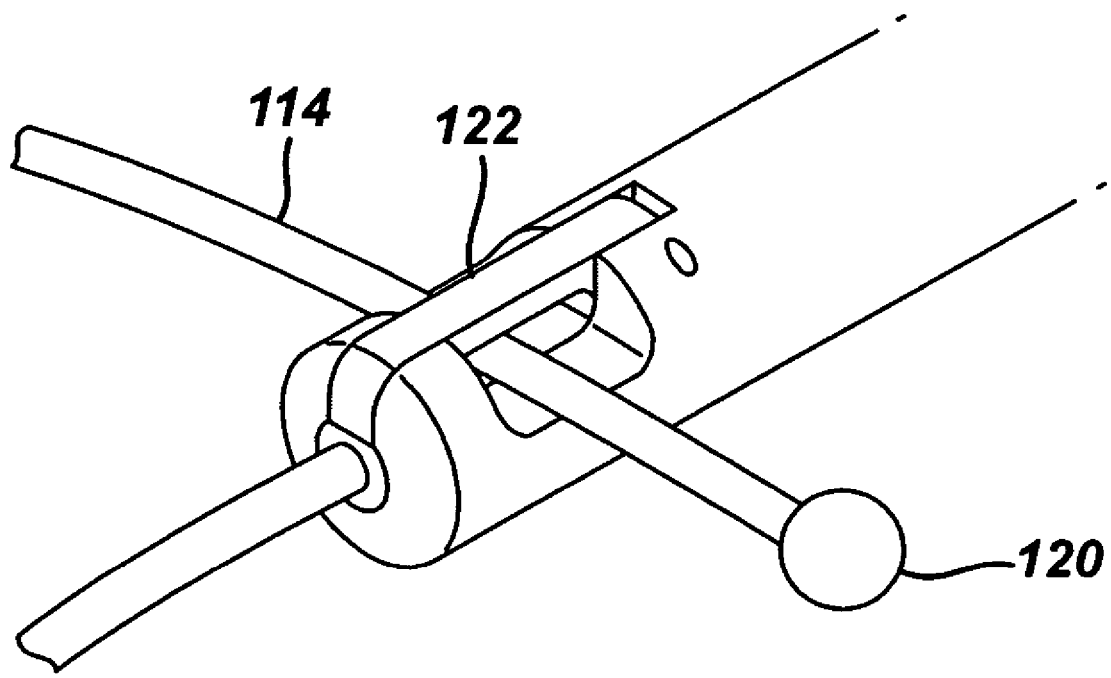
FIG. 3b is a perspective view of the distal end of the electrosurgical instrument of FIG. 1 with the electrosurgical wire in a fully deployed position, and the capture arm in the closed position.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

One embodiment of an electrosurgical instrument or lasso according to the present disclosure can be seen in FIGS. 1–3b. The electrosurgical instrument 100 includes an introducer 102 having a distal end 104 and a proximal end 106. The introducer introducer 102 may include a handle portion 108 and a shaft extension portion 110 of a smaller diameter. The shaft extension portion preferably has a length of approximately 32 cm and a maximum outer diameter of 5 mm, which will allow it to be passed through a surgical trocar. The handle portion 108 preferably will remain outside of the body and is used by the surgeon to manipulate the positioning of the extension shaft and electrosurgical wire as will be described in more detail below. The introducer 102 further has a channel therein (not shown) extending to an opening 112 at the distal end of the introducer. Although in the illustrated embodiment the opening 112 is positioned at the extreme distal end, it is also envisioned that the opening may be located on a lateral side of the extension shaft at its distal end, as shown in FIG. 1a. Thus, the phrase "an opening at a distal end" is intended to encompass both embodiments, and any other embodiment where the opening for the electrosurgical wire is present in the distal end region of the extension shaft.

The channel is dimensioned to slidably receive therein, an electrosurgical wire 114, also having a distal end 116 and a proximal end positioned within the channel. In a preferred embodiment, the electrosurgical wire loop has a diameter of approximately 3 cm, and a length of approximately 15–20 cm, with a wire thickness of approximately 0.1 to 0.5 mm. One of a pair of electrical wires 140, 141, is electrically coupled to the electrosurgical wire 114, and extends from the electrosurgical instrument for coupling with an RF energy source for applying RF energy to the electrosurgical wire. The other of the pair of electrical wires operates as a return electrode for the electrosurgical lasso, and is therefore coupled to a return electrode on the electrosurgical instrument. This return electrode may be a conductive patch or portion of any configuration positioned toward the distal end of the extension shaft, as illustrated by numeral 121 in FIG. 1a. In the alternative the entire extension shaft could be comprised of a conductive material to operate as the return electrode. In yet another embodiment, the electrosurgical wire could be segmented so that a distal portion 127 (see FIG. 1a) is the return electrode and the remaining portion 127 (other than an insulating portion 129 therebetween) is the active electrode. Numerous possibilities exist for positioning of the return electrode, as will be readily apparent to those skilled in the art.

The electrosurgical instrument further includes a deployment device or element 118 that is movably coupled to introducer and movable between a first position shown in FIG. 2, and a second position shown in FIG. 3. In the illustrated embodiment, the deployment device is slidably engaged with the handle portion 108, and extends through a slotted opening or groove 119 therein. The deployment device is slidably coupled to the handle portion by any suitable means, such as an inner flange (not shown) such that it is free to slide within the groove while remaining coupled to the handle.

The deployment device is further coupled to the proximal end of the electrosurgical wire 114 in any suitable manner, such as by welding, epoxy or any standard method of mechanical fixation, so that movement of the deployment device between the first and second positions causes corresponding movement of the electrosurgical wire within the channel. More specifically, referring to FIGS. 2 and 3, when the deployment device is in the first position (FIG. 2), the electrosurgical wire is in an undeployed or retracted position wherein it is positioned substantially entirely within the channel. As the deployment device is moved from the first to the second position, the electrosurgical wire is advanced outwardly from the opening 112 at the distal end of the channel by a corresponding amount until it reaches its fully deployed position shown in FIG. 3. As will be described in more detail below, the electrosurgical wire is preferably formed of a shape memory metal, such as nitinol, so that it assumes a predetermined configuration when fully deployed from the introducer.

A protrusion 120 at the distal end of the electrosurgical wire, such as a knob, bulb or the like, may be provided to prevent the electrosurgical wire from being retracted entirely within the channel. This protrusion may also be shaped so as to form an atraumatic tip while the wire is deployed within the body, and may also be used to assist in capturing and holding the distal end of the electrosurgical wire by the capture arm, as will be described further below. Alternate embodiments are also contemplated in which this knob element is not necessary. In such embodiments the diameter of the electrosurgical wire is sufficient so that, when captured by the capture arm, it forms an interference fit between the recess and the capture arm (also described further below). In one embodiment, a distal end portion 116 of the electrosurgical instrument is insulated to ensure that RF energy is applied only in the vicinity of the organ to be transected.

Also present at the distal end of the introducer is a capture element 122 that is movable relative to the introducer between a closed position (FIGS. 2a, 3b) and an open position (FIG. 3a). Preferably, the capture element is pivotably coupled to the introducer, and is mechanically coupled by any suitable means (such as by a standard coupling rod mechanism) to a capture element actuator 124 positioned more proximally along the introducer. In the illustrated embodiment, the capture element actuator is a sliding element positioned at the distal end of the hollow tube portion of the introducer. The capture element actuator is also movably coupled to the introducer, and movable between first and second positions (shown in FIGS. 1 and 3 respectively), wherein movement between the first and second positions causes the capture element to move between the closed and open positions respectively. Although the present embodiment is described and illustrated as having a pivotable capture element, other embodiments of a capture element are also contemplated so long as the capture element functions to grasp the distal end of the electrosurgical wire to enable cinching of the wire. For example, the capture element could simply be a groove or recess into which the distal end of the electrosurgical wire can be press fit.

Preferably, the distal end of the introducer further has a recess or grove 126 therein that is positioned relative to the capture element so that the capture element, when in the closed position, extends over the groove as shown in FIG. 2a with a space 128 therebetween. The space is of sufficient size to that the distal end of the electrosurgical wire can be positioned therein, and the capture element subsequently closed to secure the distal end of the electrosurgical wire to the introducer, as will be described further below.

In the illustrated embodiment, the distal end of the handle portion 108 further includes a rotatable knob element 131. This knob element is fixedly secured to the shaft extension portion 110 for rotation therewith, but rotatable independent of the handle portion. Further, when the knob element and shaft extension portion rotate, they do so independently of the electrosurgical wire extending through the channel therein. In this manner, the knob and shaft extension can be rotated to assist in capturing the distal end of the wire within the recess 126 and by the capture arm 122.

The electrosurgical instrument and its operation will now be described in greater detail with reference to FIGS. 4a–4e. Preparation for the procedure initially involves placement of a uterine manipulator and catheterization of the bladder. The surgical approach can be through the usual laparoscopic portals; a primary portal for the optic and two or three secondary portals for instruments, including the present electrosurgical instrument. Treatment of the round ligaments and adnexae follows standard hysterectomy technique. The broad ligament and vesicouterine fold are dissected down to the superior cervix. Prior to applying the electrosurgical wire or loop of the presently described electrosurgical instrument, the uterine vessels are dissected and sectioned after occluding them with bipolar coagulation or placement of sutures. Treatment of the uterine arteries in this fashion corresponds to a type III procedure according to the Munro-Parker classification system (see Munro, M. G., Parker, W. H.: A Classification for Laparoscopic Hysterectomy, *Obstetrics and Gynecology*, 1993; 82: 624–629). Once the uterine arteries have been cut, it is important to remove any manipulating device that has been placed in the uterus.

Figure 4A:
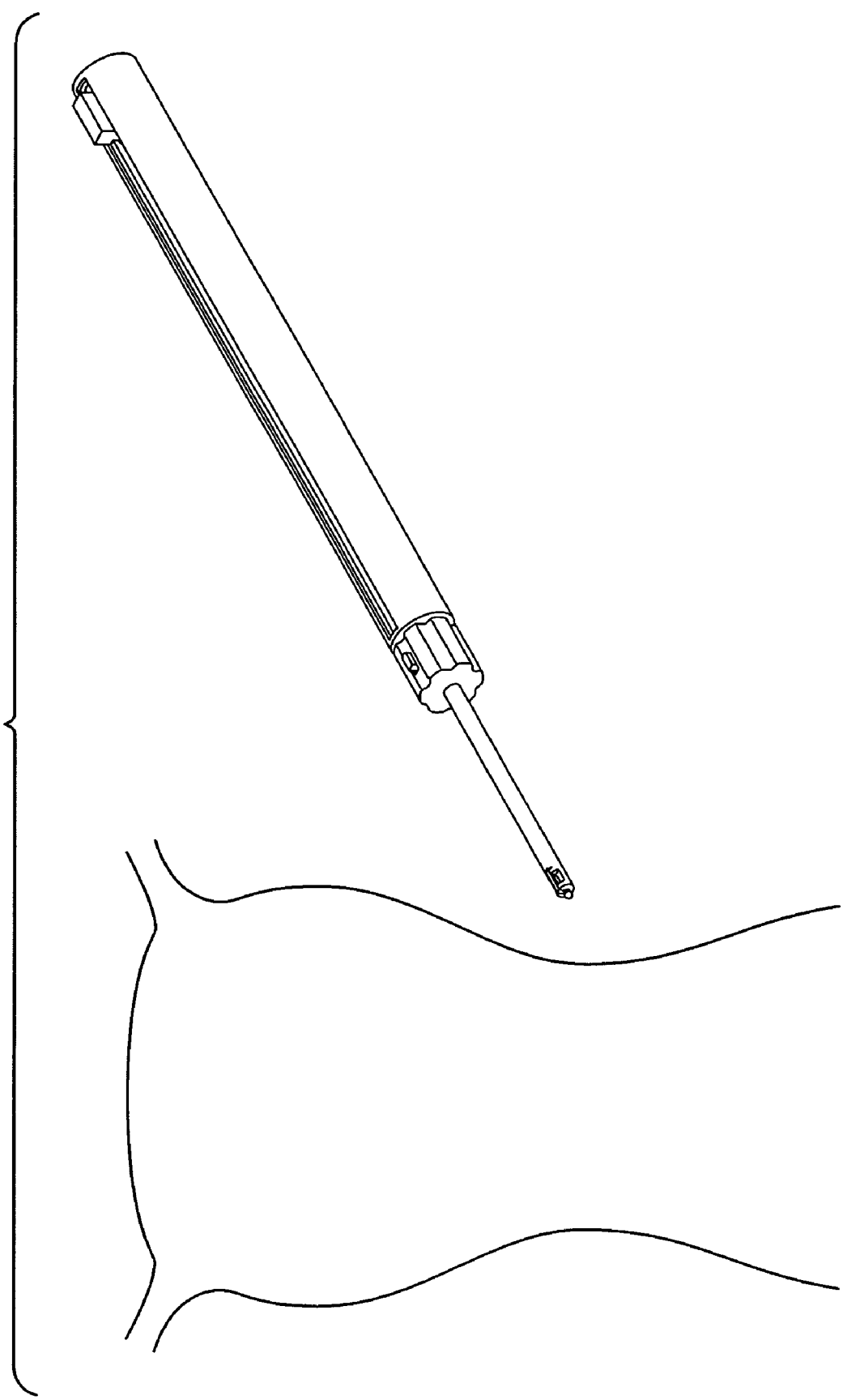
FIGS. 4a–4e illustrate various steps in a method for using the electrosurgical instrument of FIG. 1.

The electrosurgical instrument 100 is then introduced in its retraced position into the abdominal cavity through a laparoscopic portal and its distal end 104 is placed at the neck of the cervix, as shown in FIG. 4*a*. Once properly positioned, the deployment device 118 is slidably moved from the first position shown in FIG. 4*a*, to the second position shown in 4*b*, which, as explained above, causes the electrosurgical wire 114 to move from the retracted position to the fully deployed position. As indicated, the electrosurgical wire is preferably comprised of a shape memory alloy, such as nitinol, and preshaped so that it will assume the substantially looped configuration shown in FIG. 4*b* when deployed. The "loop" should be large enough so that as it is deployed it encircles the area of the organ to be transected, such as the illustrated cervical neck. During this step the capture element 122 is moved, via the capture element actuator 124, from the closed to the open position.

Figure 4B:
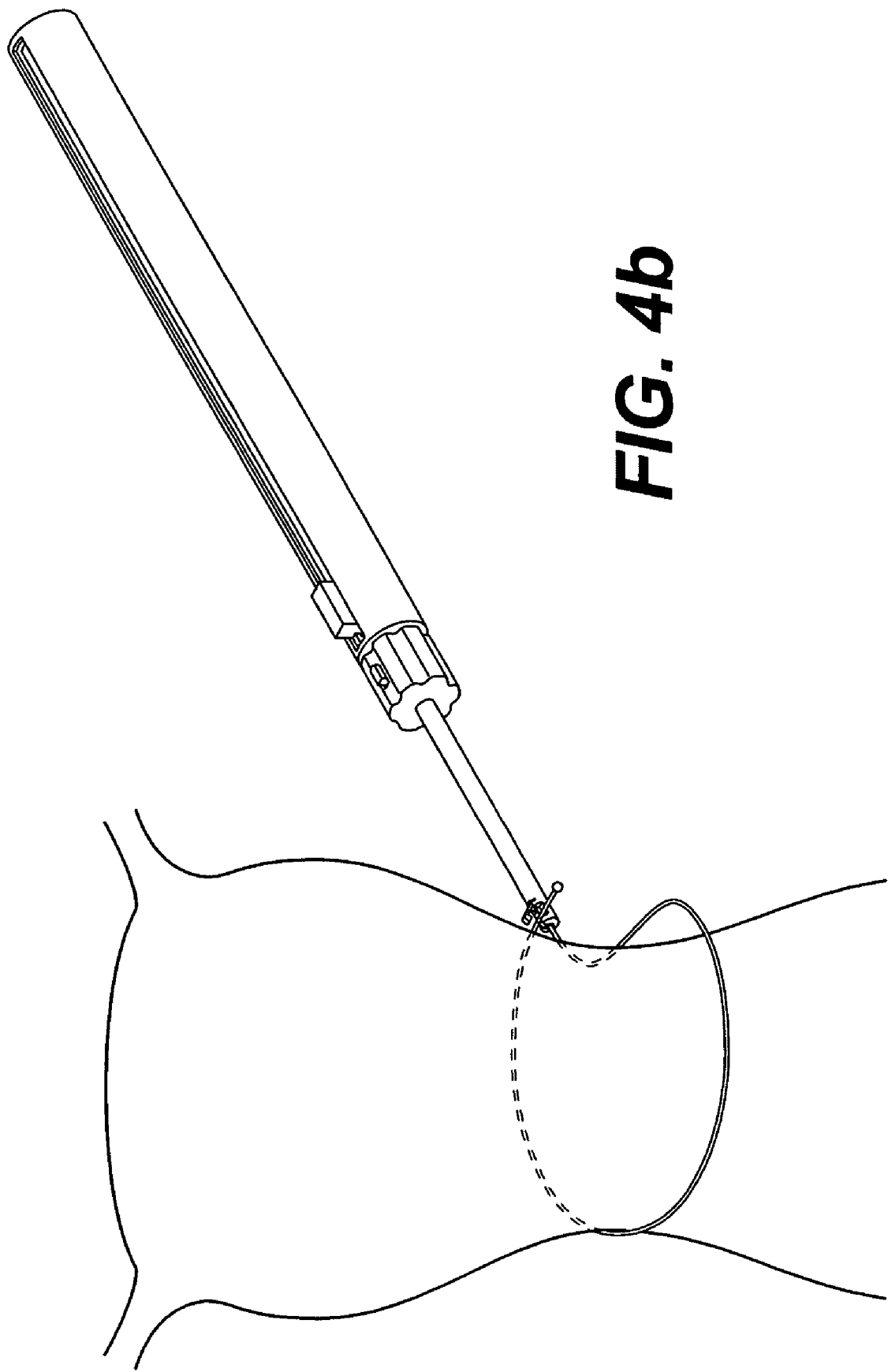
Figure 4C:
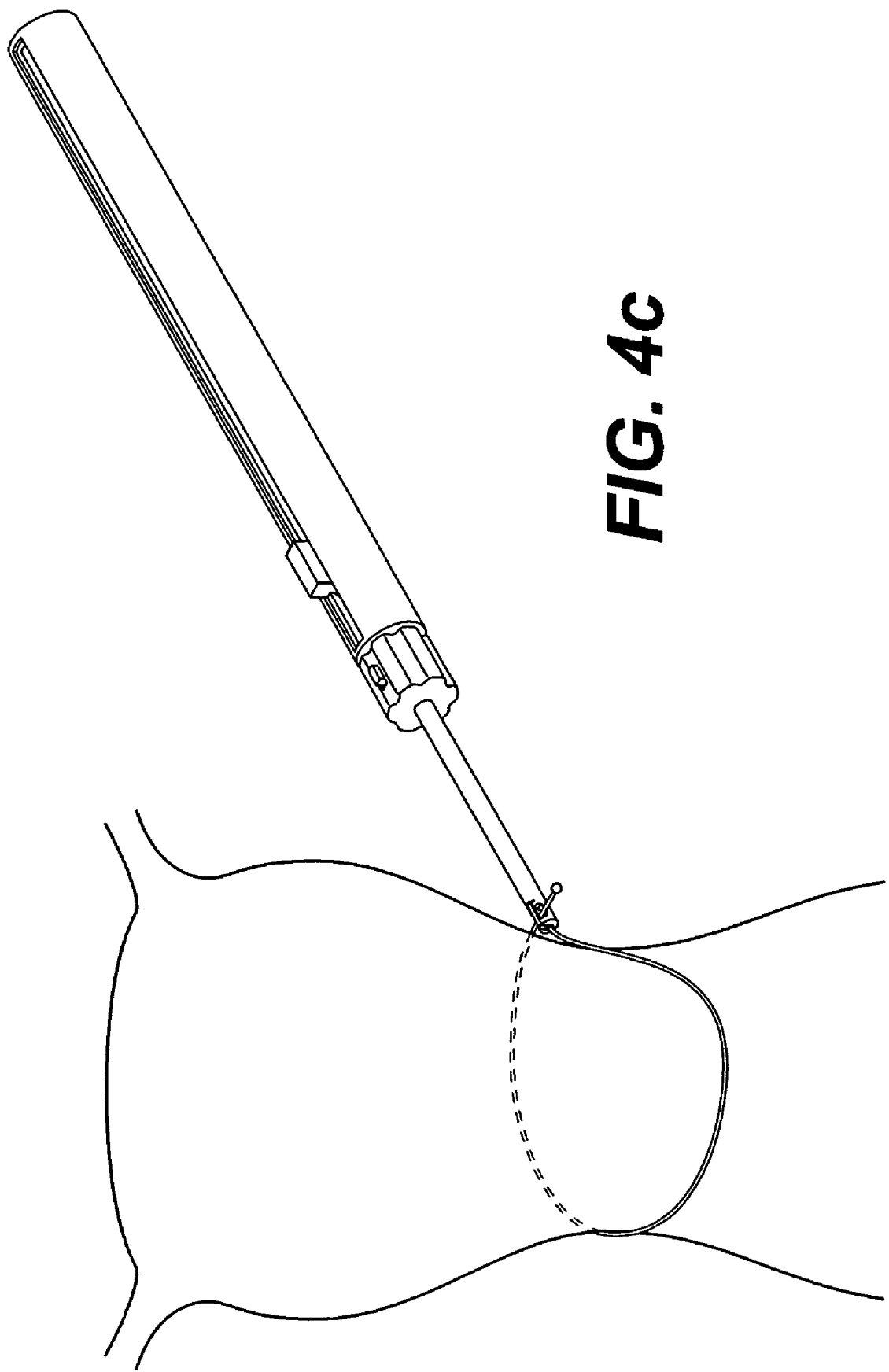

Once the electrosurgical wire is fully deployed, the shape memory nature of the electrosurgical wire should cause the distal end 116 of the electrosurgical wire to be in proximity to the capture element as shown in FIG. 4*b*. Knob 131 may then, if necessary, be rotated to thereby rotate the extension shaft 110 independently of the electrosurgical wire to aid in positioning the distal end of the electrosurgical wire within recess 126. The capture element is then moved from the opened to the closed position to thereby secure the distal end of the electrosurgical wire to the introducer, as shown in FIG. 4*c*. Before the loop is completely tightened around the cervix as will be described below, the orientation of the electrosurgical wire can be adjusted to accurately position the wire so that no unwanted endometrial tissue is left behind, and to also ensure that the cervical neck is cut as transversely as possible.

Figure 4D:
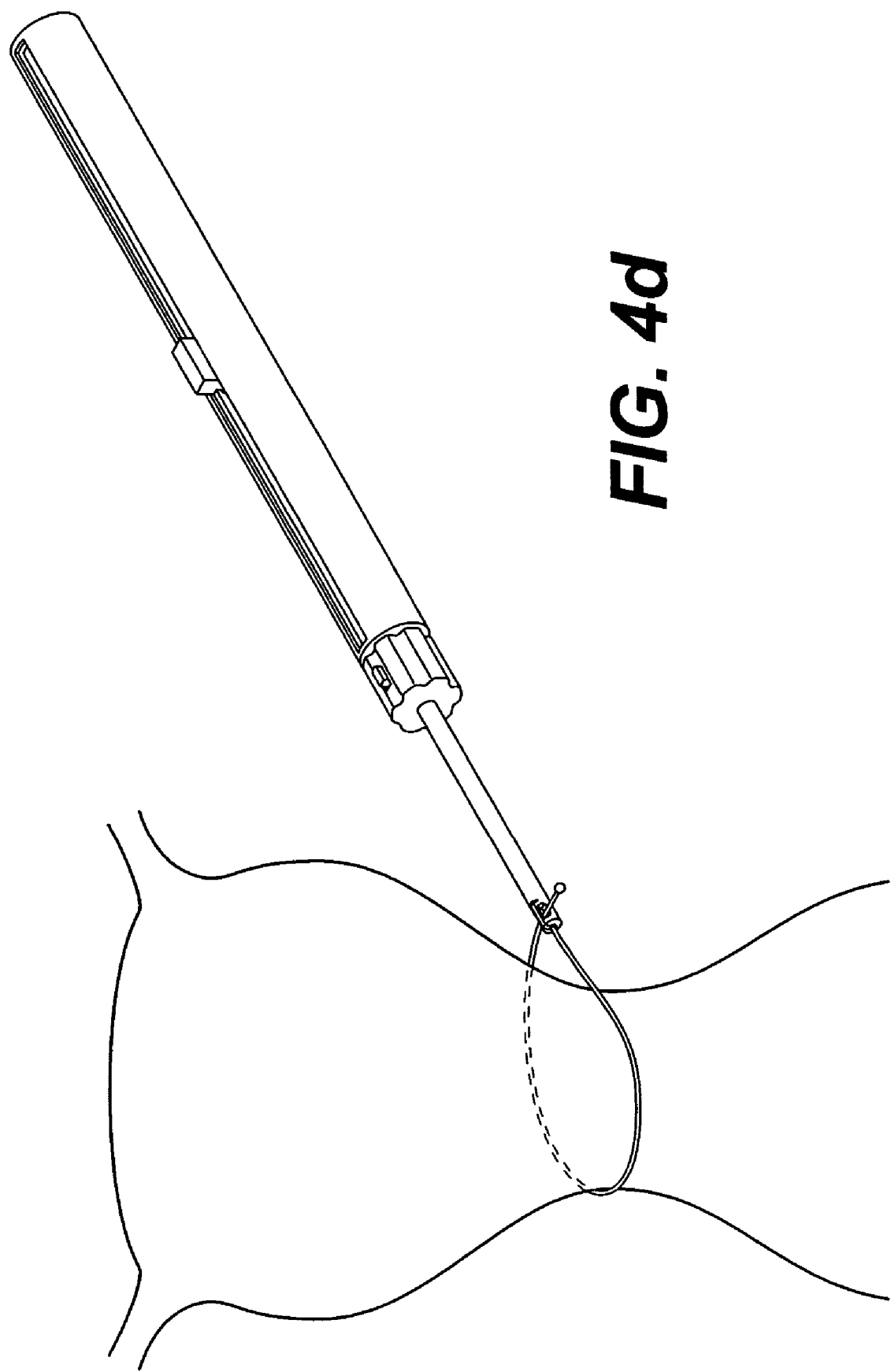
Figure 4E:
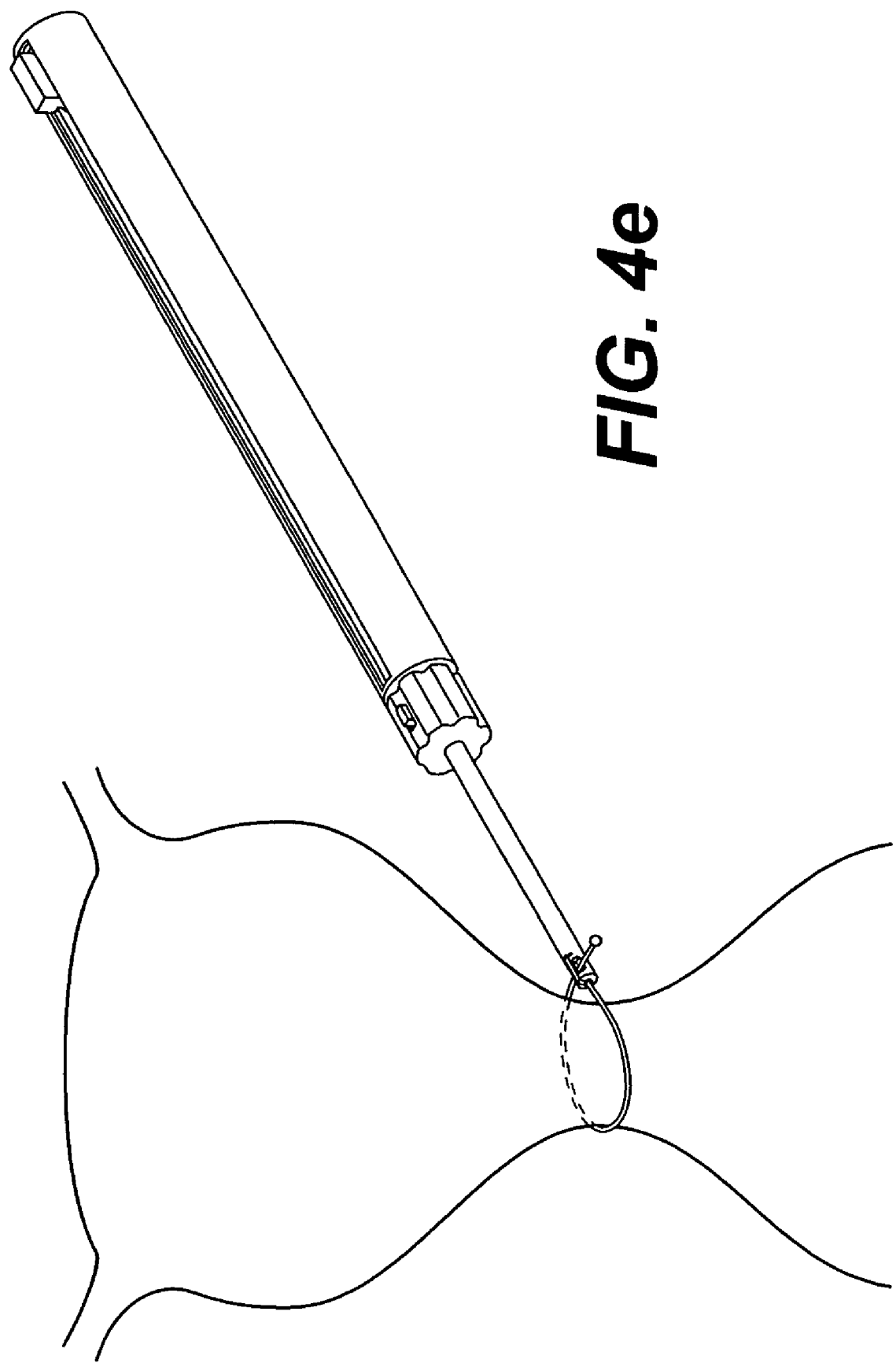

RF energy is then applied to the electrosurgical wire, and the deployment device subsequently moved from the second position toward the first position to cause the electrosurgical wire to start to be retracted again into the introducer as shown in FIGS. 4*d* and 4*e*. The design of the electrosurgical instrument is such that the cervical neck becomes cinched within the electrosurgical wire and is transected and coagulated due to the RF energy applied through the electrosurgical wire. Often it is necessary to pause the section to remove smoke and maintain good vision during amputation. After the cervix has been cut, any residual bleeding may be treated with bipolar coagulation if necessary.

Because the cervical neck is cinched as opposed to having to pull the entire energized wire against it in a unidirectional manner, there is very little unidirectional force exerted on it, and therefore, very little movement of it and surrounding organs. Thus, the cervical neck and uterus remain stabilized during the procedure.

Once the transection is complete, the capture element can be moved back to the open position, the electrosurgical wire completely retracted, and the capture element moved back to the closed position to allow the electrosurgical instrument to be removed entirely from the surgical site.

Thus, by using the electrosurgical instrument of the present invention, transection can be performed quickly and with little disruption or movement of the cervical neck and surrounding organs, and with better accuracy and reliability in transecting at the desired location.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. An electrosurgical instrument for transecting an organ, comprising:

an introducer having a distal end, a proximal end, a channel therein extending to an opening at the distal end, and a capture element at the distal end;

a conductive wire slidably receivable within the channel and movable between an undeployed position wherein the conductive wire is substantially positioned longitudinally along the length of and within the channel and wherein a distal end thereof is not secured to the introducer by the capture element, and a deployed position wherein the conductive wire extends outwardly from the distal end of the channel, and wherein its distal end is secured to the introducer by the capture element to thereby form a substantially looped configuration;

a deployment device movably coupled to the introducer and movable between a first position and a second position, the deployment device being engaged with the conductive wire such that movement of the deployment device between the first and second positions causes the conductive wire to move between the undeployed and deployed positions;

wherein, when the conductive wire is in the deployed position with the distal end of the conductive wire secured to the introducer by the capture element, the deployment device is movable toward the first position to thereby cinch the conductive wire substantially without moving the introducer or the distal end of the conductive wire, and wherein the capture element is movable between an open position and a closed position, the instrument further comprising a capture element actuator coupled with the capture element and movably coupled with the introducer, the capture element actuator being movable between first and second positions wherein such moving causes the capture element to move between the closed and open positions respectively.

2. The electrosurgical instrument according to claim 1, wherein the electrosurgical instrument is a bipolar instrument and the introducer further includes a conductive portion, and wherein the conductive wire is an active electrode and the conductive portion of the introducer is a return electrode.

3. The electrosurgical instrument according to claim 2, further comprising a bipolar generator having a first pole electrically coupled to the active electrode and a second pole electrically coupled to the return electrode.

4. The electrosurgical instrument according to claim 1, wherein the conductive wire is made from a shape memory alloy.

5. The electrosurgical instrument according to claim 4, wherein the conductive wire is further comprised of nitinol.

6. The electrosurgical instrument according to claim 1, wherein the conductive wire is comprised of a spring steel.

7. The electrosurgical instrument according to claim 1, wherein the actuator element pivots about a pivot point to move between the open and closed positions.

8. The electrosurgical instrument according to claim 7, wherein the distal end of the introducer further comprises a recess therein positioned relative to the capture element so that the capture element extends over the recess when in the closed position.

9. The electrosurgical instrument according to claim 8, wherein when the distal end of the conductive wire is secured to the introducer by the capture element, it is positioned within the groove.

10. The electrosurgical instrument according to claim 1, wherein the introducer has a groove therein along a portion of its length, and wherein the deployment device is slidably positioned within said groove.

11. The electrosurgical instrument according to claim 1, wherein the conductive wire further comprises a protrusion at the distal end.

12. An electrosurgical instrument for transecting an organ, comprising:
    an introducer having a distal end, a proximal end, a channel therein extending to an opening at the distal end, and a capture element at the distal end;
    a conductive wire slidably receivable within the channel and movable between an undeployed position wherein the conductive wire is substantially positioned longitudinally along the length of and within the channel and wherein a distal end thereof is not secured to the introducer by the capture element, and a deployed position wherein the conductive wire extends outwardly from the distal end of the channel, and wherein its distal end is secured to the introducer by the capture element to thereby form a substantially looped configuration;
    a deployment device movably coupled to the introducer and movable between a first position and a second position, the deployment device being engaged with the conductive wire such that movement of the deployment device between the first and second positions causes the conductive wire to move between the undeployed and deployed positions;
    wherein, when the conductive wire is in the deployed position with the distal end of the conductive wire secured to the introducer by the capture element, the deployment device is movable toward the first position to thereby cinch the conductive wire substantially without moving the introducer or the distal end of the conductive wire, and
    wherein the introducer further comprises shaft extension portion having a first diameter and a handle portion adjacent the shaft extension portion having a second diameter greater than the first diameter, and wherein the channel extends through the shaft extension portion and into the handle portion.

13. A bipolar electrosurgical instrument for transecting an organ, comprising:
    an introducer having a distal end, a proximal end, a channel therein extending to an opening at the distal end, and a capture element at the distal end, the introducer having a conductive portion forming a return electrode;
    a conductive wire comprised of a shape memory alloy slidably receivable within the channel and movable between an undeployed position wherein the conductive wire is substantially positioned longitudinally along the length of and within the channel and wherein a distal end thereof is not secured to the introducer by the capture element, and a deployed position wherein a portion of the conductive wire is deployed from and positioned outside of the introducer with its distal end being secured to the introducer by the capture element to thereby form a substantially looped configuration, the conductive wire forming an active electrode;
    a deployment device movably coupled to the introducer and movable between a first position and a second position, the deployment device being engaged with the conductive wire such that movement of the deployment device between the first to second positions causes the conductive wire to move between the undeployed and deployed positions respectively;
    wherein, when the conductive wire is in the deployed position with the distal end of the conductive wire is secured to the introducer by the capture element, the deployment device is movable toward the first position to thereby cinch the conductive wire substantially without moving the introducer or the distal end of the conductive wire, and
    wherein the capture element is movable between open and closed positions, the instrument further comprising a capture element actuator coupled with the capture element and movably coupled with the introducer, the capture element actuator being movable between first and second positions wherein moving between the first and second positions causes the capture element to move between the closed to open positions respectively.

14. The electrosurgical instrument according to claim 13, further comprising a bipolar generator having a first pole electrically coupled to the active electrode and as second pole electrically coupled to the return electrode.

15. The electrosurgical instrument according to claim 13, wherein the distal end of the introducer further comprises a recess therein positioned relative to the capture element so that the capture element extends over the recess when in the closed position, and wherein when the distal end of the conductive wire is secured to the introducer by the capture element, it is positioned within the recess.

* * * * *